(12) United States Patent
Kamada et al.

(10) Patent No.: US 8,142,090 B2
(45) Date of Patent: Mar. 27, 2012

(54) COSMETIC PRODUCT AND METHOD OF APPLYING A MASCARA COMPOSITION

(75) Inventors: Kenji Kamada, Hikone (JP); Keiko Funatsu, Hikone (JP); Naoki Yamaguchi, Hikone (JP); Satoru Hatano, Ashiya (JP); Ann Virginia Lam, Cincinnati, OH (US)

(73) Assignees: Panasonic Corporation, Osaka (JP); The Procter & Gamble Company, Cincinnati, OH (US)

( * ) Notice: Subject to any disclaimer, the term of this patent is extended or adjusted under 35 U.S.C. 154(b) by 1357 days.

(21) Appl. No.: 11/667,314

(22) PCT Filed: Nov. 24, 2005

(86) PCT No.: PCT/JP2005/022047
§ 371 (c)(1),
(2), (4) Date: May 9, 2007

(87) PCT Pub. No.: WO2006/057439
PCT Pub. Date: Jun. 1, 2006

(65) Prior Publication Data
US 2007/0286831 A1    Dec. 13, 2007

(51) Int. Cl.
*A46B 11/08*  (2006.01)
(52) U.S. Cl. ............... 401/1; 401/2; 401/118; 132/218
(58) Field of Classification Search ........ 401/1, 2, 401/3, 118, 119, 129; 132/218, 216, 119.1; 15/25, 26, 34
See application file for complete search history.

(56) References Cited

U.S. PATENT DOCUMENTS

| | | | |
|---|---|---|---|
| 1,939,566 A * | 12/1933 | Melendez | 401/78 |
| 5,876,704 A | 3/1999 | Collin et al. | |
| 6,026,824 A * | 2/2000 | Gueret | 132/218 |
| 6,413,496 B1 | 7/2002 | Goodman et al. | |
| RE38,362 E | 12/2003 | Collin et al. | |
| 7,090,420 B2 * | 8/2006 | De La Poterie et al. | 401/1 |

(Continued)

FOREIGN PATENT DOCUMENTS

EP    1 466 541 A1    10/2004

(Continued)

OTHER PUBLICATIONS

Written Opinion of the International Searching Authority (5 Sheets.).

(Continued)

*Primary Examiner* — David J. Walczak
*Assistant Examiner* — Jennifer C Chiang
(74) *Attorney, Agent, or Firm* — Cheng Law Group, PLLC

(57) ABSTRACT

A cosmetic product includes a mascara composition and a treatment device, whereby the mascara composition is applied to the eyelashes by softening the mascara composition via heat. The mascara composition is solid at room temperature, however is softened at elevated temperature, so it may be applied to the eyelashes. The treatment device includes an applicator for receiving, heating to soften, and applying the softened mascara composition to the eyelashes. Once the softened mascara composition is applied to the eyelashes, the mascara composition is quickly cooled and thus solidified by the atmosphere. The mascara composition thus applied to the eyelashes provides a firm film covering the eyelashes, which is not softened at body temperature, and thus provides enhanced wearability. A cap detachable to the applicator is provided with a loading mechanism for delivering pieces of the mascara composition one by one to the applicator.

14 Claims, 8 Drawing Sheets

U.S. PATENT DOCUMENTS

| | | |
|---|---|---|
| 2001/0002228 A1 | 5/2001 | Owens |
| 2005/0150509 A1* | 7/2005 | Gueret .......................... 132/217 |
| 2006/0112503 A1* | 6/2006 | Hatano et al. ..................... 8/406 |

FOREIGN PATENT DOCUMENTS

| | | |
|---|---|---|
| JP | 3285799 B2 | 3/2002 |
| WO | WO 99/22782 A2 | 5/1999 |

OTHER PUBLICATIONS

Notification of Reasons for Refusal for the Application No. 2007-523440 from Japan Patent Office mailed Aug. 3, 2010.

* cited by examiner

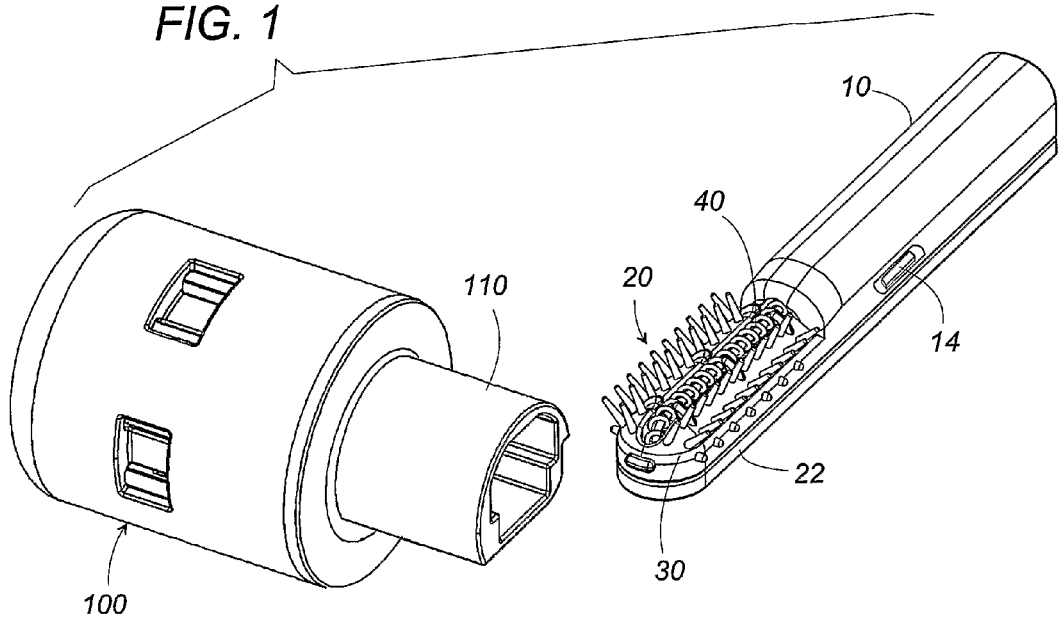
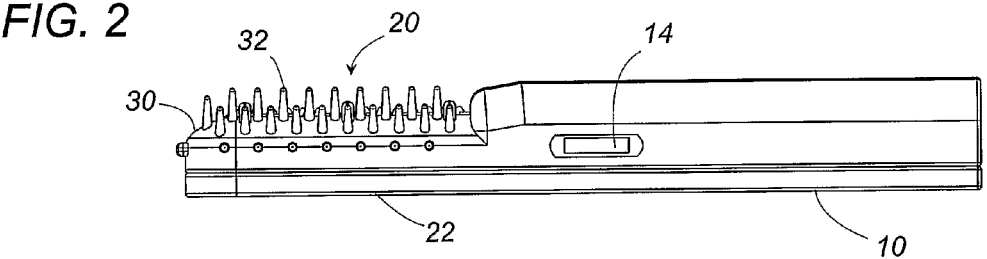
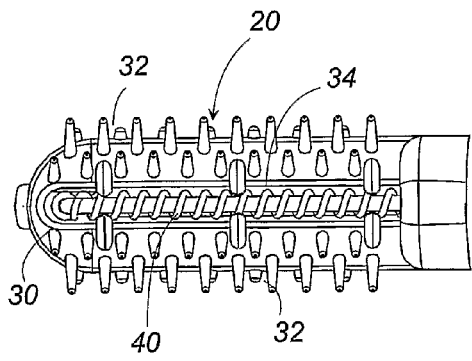
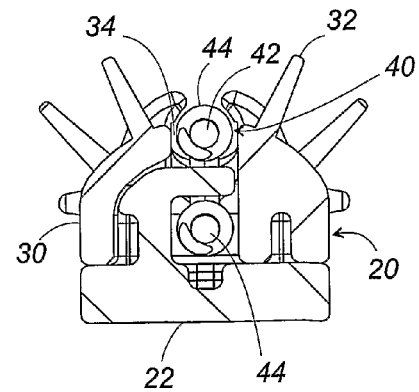

COSMETIC PRODUCT AND METHOD OF APPLYING A MASCARA COMPOSITION

TECHNICAL FIELD

The present invention relates to a cosmetic product including a mascara composition and an eyelash treatment device, whereby the mascara composition is applied to the eyelashes by fluidizing the mascara composition via heat generated by the eyelash treatment device. The product provides improved performance of a mascara composition, while also being safe for the general consumer to use. The present invention further relates to a method of applying a mascara composition to the eyelashes.

BACKGROUND ART

Mascara products are used to enhance the beauty of a person's eyes by coating the eyelashes to primarily thicken, lengthen, color, and define the individual eyelashes. For the last 60 years, mascara products have been provided in the form of mascara applicators having an applicator brush attached to a handle, the applicator brush portion dipped in a package, such as a tube, containing a liquid to semi-solid mascara composition. Mascara compositions typically take the form of emulsions or dispersions of waxes and pigments in water or other volatile carriers. Mascara composition and delivery systems are limited by emulsion or solution chemistry and film forming technologies that are applied wet and then dried to create a film of mascara that sets and holds the eyelashes.

These mascara compositions which are liquid to semi-solid have a low viscosity profile and low yield point, such that they are inherently prone to smearing and smudging after application to the eyelashes. The solid components dispersed in the composition, such as waxes, may also be difficult to apply, as clumping and globbing may occur due to lack of film smoothness of the solid components.

From another aspect, solvents and carriers of the composition that do not evaporate in timely manner may also provide smearing and smudging after application to the eyelashes. The so-called waterproof mascaras intend to solve such problem by employing volatile hydrocarbon solvents. While such volatile hydrocarbon solvents provide wear benefits, the application and beauty benefits may be compromised. Further, the volatile hydrocarbon solvents may cause odor and safety concerns.

One solution for providing a mascara composition having improved application and improved wearability, is to provide the composition solid, wherein the composition is heated prior to application to the eyelashes, for softening, and/or smoothing the composition upon application. Such heating would also benefit in shortening the evaporation time required after application. The solid film provided on the eyelashes after application would have a much higher yield point than films made by conventional mascara compositions, thereby being less prone to smearing and smudging.

Based on the foregoing, there is a need for a mascara product which can apply a solid mascara composition to the eyelashes in a safe and effective manner. It would be further beneficial to provide the solid mascara composition in a pre-determined dosage form, such that the user is easily provided with an adequate amount of composition to apply to the eyelashes.

Meanwhile, there have been proposed in the art eyelash curling devices, such as WO 99/22782 including a applicator brush and heater combination. However, the applicator brush is designed to curl the eyelashes by application of heat, while applying the mascara composition of liquid or semi-liquid condition fetched from a container. Due to the absence of the idea and structure for heating and fluidizing the solid mascara composition, the applicator brush is practically impossible to use in combination with the mascara composition proposed by the present invention. There is a need of providing a dedicated treatment device which takes the full benefit of the mascara composition to apply the fluidized composition successfully and uniformly to the eyelashes. There is a further need of providing such a treatment device which also comprises a loading means for providing a predetermined dosage form of mascara composition upon use.

None of the existing art provides all of the advantages and benefits of the present invention.

DISCLOSURE OF THE INVENTION

The present cosmetic product comprises a mascara composition and an eyelash treatment device, whereby the mascara composition is applied to the eyelashes by softening the mascara composition via heat, the applied mascara composition forms a solid film on the eyelashes, which film has improved wearability. The product provides improved performance of a mascara composition, while also being safe for the general consumer to use.

The mascara composition is solid at room temperature, however is softened at elevated temperature, so it may be applied to the eyelashes. The eyelash treatment device comprises a heater for providing enough heat to the mascara composition, yet safe for application to the eyelashes, even in accidental situations where the user inadvertently touches the device with the eyelids or eyeballs. The eyelash treatment device comprises an applicator for receiving, heating (softening), and applying the mascara composition.

Once the softened mascara composition is applied to the eyelashes, the mascara composition is quickly cooled and thus solidified by the atmosphere. The mascara composition thus applied to the eyelashes provides a firm film covering the eyelashes, which is not easily softened at body temperature, and thus provides enhanced wearability.

In particular, the mascara composition of the present invention fulfills the above performances by incorporation of a solid hydrophobic component which gives a unique rheological profile to the composition. The rheological profile of the composition is defined in terms of a needle penetration as measured according to ASTM (American Society for Testing and Material) Test Method D5, a yield stress, and a viscosity. The mascara composition of the present invention is prepared to have the needle penetration of from about 1 to about 40, the yield stress of at least about 1500 Pa at 25° C., and the viscosity of between about 1 mPas and about 10,000,000 mPas at 100° C. The mascara composition with the above rheological profile can be therefore applied to the eyelashes by being softened via heat and is then solidified on the eyelashes to provide a firm film on the eyelashes.

The mascara composition may be prepared in the form of an oil mixture in which the solid hydrophobic component forms an oil phase. The composition may be alternatively in the form of a water-in-oil emulsion additionally including water and an emulsifier.

Further, the composition may be added with a pigment and/or a film forming polymer for enhanced aesthetic appeal and wearability.

The device of the present invention is specifically designed to give a structure that is configured to soften the mascara composition and to hold the softened mascara composition for applying it to the eyelashes uniformly. The device includes an applicator equipped with a heater for softening the mascara composition, and a comb arranged along the length of the applicator. The comb is arranged along the length of the applicator to be coated with the softened mascara composition. Whereby the softened mascara composition can be successfully delivered to the eyelashes from the entire length of the comb, leaving the solid mascara film on the eyelashes.

The device of the present invention is further equipped with a loading means for delivering a predetermined dosage form of mascara composition upon use. The loading means may be provided in a cap fitted over the applicator. By providing the device with the loading means of predetermined dosage, the user may easily apply an adequate amount of composition to the eyelashes. The loading means is configured to hold a plurality of mascara pieces and to load the mascara piece one by one to the applicator for delivering the adequate dosage of the mascara composition.

The cap includes a sheath fitted over the applicator and formed with an opening communicating with the applicator. The loading means includes a carrier which has a plurality of compartments each storing the mascara piece. The carrier is movable relative to the sheath in order to make one of the compartments selectively in registration with the opening for delivering the mascara piece to the applicator through the opening. Thus, the mascara piece can be easily delivered to the applicator simply by manipulating the carrier.

Preferably, the carrier is prepared in the form of a sleeve coaxial with the sheath to be rotatable about the axis of the sheath. In this instance, the sleeve may be equipped with a plurality of gates which normally close the compartments and are movable to open the associated compartments for delivering the mascara piece.

The opening may be provided with a normally-closed valve. In this instance, the loading means is provided with a plunger which forces the mascara piece to temporarily open the flap valve for delivering the mascara piece to the applicator.

The carrier may take the form of a disc which is rotatable about an upright axis perpendicular to the axis of the sheath, and has a plurality of compartments arranged about the upright axis. Also with this arrangement, the mascara piece can be delivered simply by rotating the disc about the upright axis perpendicular to the axis of the sheath or the applicator.

The mascara piece may be retained in each of the compartments by means of a breakable seal. In this connection, the loading means is provided with a plunger which forces the mascara piece out of the breakable seal for delivering the same to the applicator. With the use of the breakable seal, the mascara composition can be kept in good condition over a long period, but is easy to be loaded to the applicator.

The compartments formed in the disc may be spaced circumferentially as well as radially such that a set of radially aligned compartments comes into registration with the opening elongated along the axis of the sheath. With this arrangement, more than one mascara piece can be delivered to axially spaced points on the applicator.

Rather than utilizing the movable carrier holding the mascara pieces, the loading means may include a feeder in the form of a screw-in piston that drives the mascara pieces linearly towards the opening with the normally-closed flap valve. The loading means is further provided with a plunger that forces the mascara piece just around the opening against the flap valve to temporarily open the valve. Thus, the mascara piece can be delivered by a combination of manipulating the feeder and the plunger.

Instead of the screw-in piston, the feeder may be in the form of a spring-biased piston so that the mascara piece can be delivered simply by pressing the plunger.

Further, the loading means may be configured to include a hopper formed at one end of the sheath away from the opening to contain the mascara pieces in the form of pellets, and a screw-conveyor extending into the compartment for feeding the pellets from the hopper to the opening. Thus, the mascara composition can be delivered simply by manipulating the screw-conveyor, and by an adequate amount or dosage by adjusting the movement of the conveyor.

These and other features, aspects, and advantages of the present invention will become evident to those skilled in the art from a reading of the present disclosure with the appended claims.

BRIEF DESCRIPTION OF THE DRAWINGS

While the specification concludes with claims particularly pointing out and distinctly claiming the invention, it is believed that the present invention will be better understood from the following description of preferred, nonlimiting embodiments and representations taken in conjunction with the accompanying drawings in which:

FIG. 1 is an exploded perspective view of an eyelash treatment device in accordance with a preferred embodiment of the present invention;

FIG. 2 is a front view of the above device;

FIG. 3 is a top view of the applicator;

FIG. 4 is a sectional view of the applicator;

DETAILED DESCRIPTION OF THE PREFERRED EMBODIMENT

Figure 5:
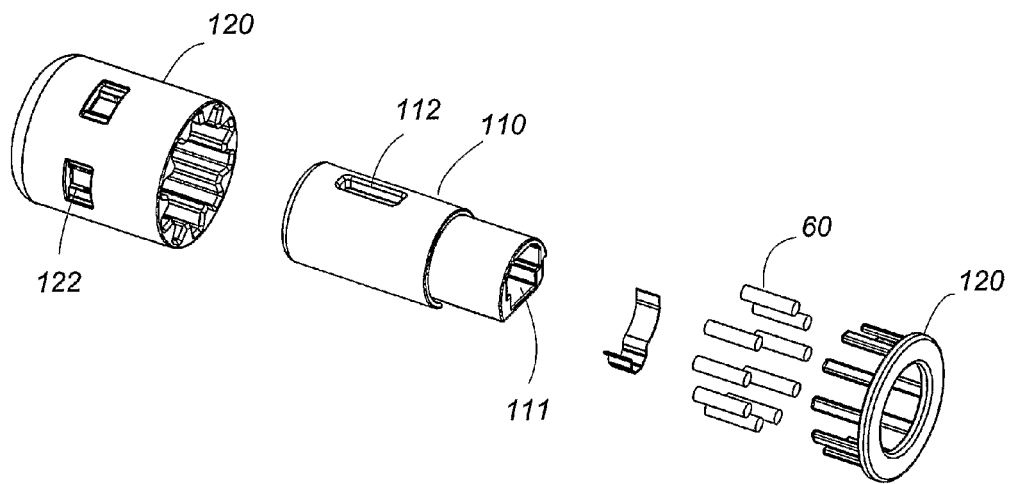
FIG. 5 is an exploded perspective view of a cap adapted in the above device for loading mascara pieces in accordance with a first embodiment of the present invention.

While the description concludes with claims particularly pointing out and distinctly claiming the invention, it is believed that the present invention will be better understood from the following description.

A product in accordance with the present invention is a combination of a mascara composition and an eyelash treatment device.

Mascara Treatment Device

Now referring to FIGS. 1 to 4, there is shown an eyelash treatment device in accordance with a preferred embodiment of the present invention. The device uses a solid mascara composition which is solid at room temperature, namely 25° C., and is softened with elevated temperature such that it can be applied to the eyelashes. By "solid" herein for describing the mascara composition, what is meant is that the composition has a certain hardness to retain its structure, and also that the composition is stable against stress or shear. The mascara composition goes through a transition change in terms of rheology between 25° C. and 100° C., such that during these temperatures, there is a range of temperature and rheology in which the composition is suitably softened for application to the eyelashes. The softened state of the mascara composition is fluid enough to be applied to the eyelashes, however, is viscous enough to stay on the applicator upon application, and on the eyelashes after application.

The device includes an elongated hand grip 10 carrying at its one longitudinal end an applicator 20 for applying the softened mascara composition to user's eyelashes. The applicator 20 is elongated to have a length generally aligned with a length of the grip 10, and includes a heater 40 which is configured to heat the mascara composition for softening the composition after it is loaded to the applicator 20 on one hand, and to heat the eyelashes for curling on the other hand. The mascara composition is provided in the form of a solid piece and is held in a cap 100 detachable to the applicator. The cap 100 is configured to include a loading mechanism for loading or delivering the mascara piece one by one onto the applicator, details of which will be discussed later.

The applicator 20 is composed of a head 22 extending integrally from the grip 10, and a comb attachment 30 detachably fitted on the head 22. The head 22 is made of a dielectric plastic material and carries the heater 40 composed of a resistor coil 42 wound around a U-shaped core 44 of dielectric material to give two parallel vertical rows running in the length of the applicator 20. The coil 42 is electrically connected to a voltage source, i.e., a battery within the grip 10 and is energized by manipulating a switch handle 14 on the side of the grip 10. The comb attachment 30 is made of a dielectric plastic material and is fitted on the head 22 in thermal transfer relation with the heater 40 so as to be heated to an elevated temperature for softening the mascara composition. The comb attachment 30 is shaped to have a rounded top face provided with a comb having a plurality of comb teeth 32 which are arranged along the length and width of the applicator for applying the softened mascara composition to the eyelashes while smoothening the eyelashes. A ditch 34 is formed in the width center of the top face to extend the length of the applicator 20 for receiving an upper part of the heater 40 and also for providing a space within which the softened mascara composition can be retained. The softened mascara composition is thereafter allowed to flow over the comb teeth, climbing-up to the comb teeth 32 by the action of a surface tension to be ready for being delivered to the eyelashes as the comb teeth 32 smoothen the eyelashes.

Figure 20:
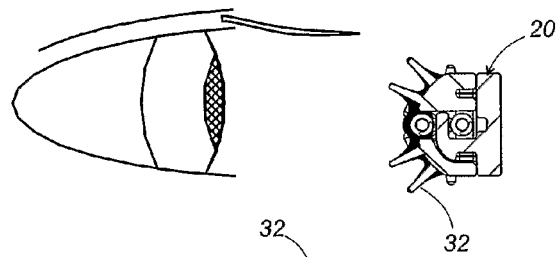
FIGS. 20 to 22 are views explaining how to apply the mascara composition while curing the eyelashes with the use of the device.
Figure 21:
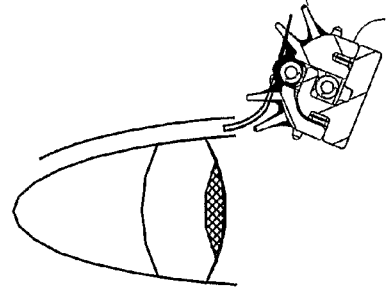
Figure 22:
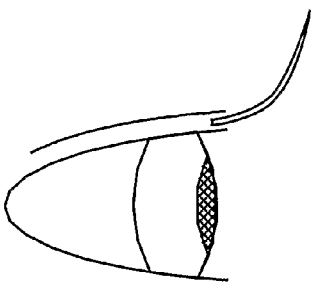

In operation, the applicator 20 is firstly placed in a position with the comb attachment 30 just below the eyelashes, as shown in FIG. 20. Then, the applicator 20 is raised and twisted to some extent for smoothing the eyelashes with the comb teeth 32, as shown in FIG. 21, thereby applying the softened mascara composition to the eyelashes, while lifting the same. In this condition, the top face of the comb attachment 30 comes into contact with the eyelashes for heating and curling the eyelashes. As soon as the applicator 20 is moved away from the eyelashes, as shown in FIG. 22, the softened mascara composition is cooled quickly to give a firm film of the solidified mascara composition on the eyelashes. Thus, the above single operation can give the effect of forming the mascara film as well as curling the eyelashes.

The heater 40 is controlled to heat the comb attachment 30 to a temperature of about 50° C. to 100° C. for softening the mascara composition. At the elevated temperature, the softened mascara composition exhibits a viscosity of 1 mPas to 10,000,000 mPas, sufficient for coating the eyelashes, but being kept from flowing out of the applicator 20 for assuring a safe application of the mascara composition.

Mascara Composition

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

The mascara composition of the present invention is solid at room temperature, namely 25° C., and is softened with elevated temperature such that it can be applied to the eyelashes. By "solid" herein for describing the mascara composition, what is meant is that the composition has a certain hardness to retain its structure, and also that the composition is stable against stress or shear. The present composition has a needle penetration, as measured according to the American Standard prescribed by the American Society for Testing and Materials (ASTM) Test Method D5, of from about 1 to about 40, and a yield stress of no less than about 1500 Pa, both measurements at 25° C., preferably at 35° C.

The principle of the measurement of the needle penetration according to the ASTM D5 consists of measuring the depth, expressed in tenths of a millimeter, to which a standard needle (weighing 2.5 g and placed in a needle holder weighing 47.5 g, i.e., a total of 50 g) penetrates when placed on the composition for 5 seconds. The principle of the measurement of yield stress consists of measuring oscillation stress sweep for understanding flow behavior and viscoelastic character for fluids and semi-solids as a function of stress, shear rate, or temperature. In the present invention, the yield stress is measured using a TA Instrument Rheometer AR-500 using a 40 mm Al Parallel Plate (Gap: 600 mm) at 1 Hz. At 25° C., the present composition preferably has no measurable yield point under stress or shear.

The mascara composition changes rheology as it is heated, and finally reaches a point where it is liquid by 100° C., preferably by 90° C. By "liquid" herein for describing the mascara composition, what is meant is that the composition has a viscosity of between about 1 mPas and about 10,000,000 mPas. The present mascara composition goes through a transition change in terms of rheology between 25° C. and 100° C., such that during these temperatures, there is a range of temperature and rheology in which the composition is suitably softened for application to the eyelashes. The softened state of the mascara composition is fluid enough to be applied to the eyelashes with an average number of strokes of an applicator holding the composition, however, is viscous enough to stay on the applicator upon application, and on the eyelashes after application. When the composition is too thin or watery, the composition is difficult to hold on the applicator, and amount of composition applied to the eyelashes decreases.

The mascara composition is designed to have a rheology profile which gives suitable rheology during the temperature band to which the eyelash treatment device is heated. The temperature band may be selected to provide suitable balance of applicability of the mascara composition and eyelash curling/lifting benefit. Typically, the temperature band is between about 50° C. and about 100° C.

The components for the composition are selected in order to provide the desired rheology profile. The composition comprises at least a solid hydrophobic component for providing the essential physical characteristics of the present invention. The composition may be made solely by the solid hydrophobic component.

The composition may take the phase form of an oil mixture, the oil being mainly made by the wax, or a water-in-oil emulsion. Water-in-oil emulsion forms are suitable for encompassing water-soluble or water-dispersible components.

Alternatively, the mascara composition may comprise an outer shell comprising at least a solid hydrophobic component having the unique rheological profiles described above, and an inner core which has a certain viscosity. The mascara composition in room temperature is in solid form encasing a fluid inner core. After heating, such embodiment composition is believed to provide an adequate crystallization time before solidifying, thereby allowing the user to have adequate time to apply and fix the composition on the eyelashes. Such longer "play time" allows the user to achieve the desired appearance of eyelashes.

The inner core may be an aqueous continuous composition containing 15% to 95% water by weight of the inner core. Such aqueous continuous phase inner core is easy to remove with soap and water. The inner core may also be an oil continuous composition containing 30% to 50% volatile liquid oil by weight of the inner core. Such oil continuous phase inner core provides waterproof benefit.

Solid Hydrophobic Component

The present composition comprises a solid hydrophobic component for providing the solid characteristic of the mascara composition. Solid hydrophobic components are typically used at levels from about 25% to about 100% in oil mixture forms, and from about 25% to about 95% in water-in-oil emulsion forms. Suitable solid hydrophobic components include waxes and fats.

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, synthetic waxes petroleum waxes, ethylenic polymers, hydrocarbon types such as Fischer-Tropsch waxes, silicone waxes, and mixtures thereof wherein the waxes have a melting point between 25° C. and 100° C.

The specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); C24-45 alkyl methicones (silicone waxes); and mixtures thereof.

Highly preferable commercially available waxes herein include stearyl palmitate by the tradename PURESTER 34, available from Strahl & Pitsch, ceresin by the tradename CERESIN 252 available from Strahl & Pitsch, and paraffin wax by the tradenames PARAFFIN SP-673P, PARAFFIN 206, and PARAFFIN 192 available from Strahl & Pitsch.

Useful herein are fats, namely glyceryl esters of higher fatty acids such as stearic and palmitic. Such esters and their mixtures are solid at room temperature and exhibit crystalline structure. The fats employed according to the invention are selected from the group consisting of fats derived from animals, vegetables, synthetically derived fats, and mixtures thereof wherein said fats have a melting point from about 55° to about 100° C. Preferably, the fats are selected from the group consisting of glyceryl monostearate, glyceryl distearate, glyceryl tristearate, palmitate esters of glycerol, C18-36 triglycerides, glyceryl tribehenate, C18-36 acid triglycerides and mixtures thereof.

Highly preferable commercially available fats herein include glyceryl monostearate by the tradename CUTINA GMS-V available from Cognis Cutina.

Pigments

The compositions of the present invention may comprise pigments selected from the group consisting of inorganic pigments, organic pigments, and organic lake pigments, pearlescent pigments, and mixtures thereof. The present invention comprises mascara compositions devoid of pigments however, as such compositions may also provide the benefits of the present invention.

When employed, the pigments are present in proportions depending on the color and the intensity of the color that it is intended to produce. When employed, the level of pigments in the composition is from about 3% to about 25%, preferably from about 5% to about 15%. The pigments may optionally be surface-treated with treatments that include, but are not limited to, silicones, perfluorinated compounds, lecithin, and amino acids.

Inorganic pigments useful in the present invention include those selected from the group consisting of rutile titanium dioxide, anatase titanium dioxide (both coded in the Color Index under the reference CI 177891); black, yellow and red iron oxides (CI 177499, 77492 and 77491); bismuth oxychloride (CI 177163); manganese violet (CI 177742); ultramarines (CI 177007); chromium oxide (CI 77288); chromium hydroxide (CI 177289); ferric ferrocyamide (CI 177510); zinc oxide (CI 177947); and mixtures thereof.

The organic pigments useful in the present invention include carbons black, and the dyes and the analogous lakes selected from the group consisting of D&C Red 6 (CI 115850); D&C Red 7 (CI 115850:1); D&C Red 21 (CI 145380:2); D&C Red 22 (CI 145380); D&C Red 27 (CI 145410:1); D&C Red 28 (CI 145410); D&C Red 30 (CI 173360); D&C Red 33 (CI 117200); D&C Red 34 (CI 115880:1); D&C Red 36 (CI 112085); D&C Orange 4 (CI 115510); D&C Orange 5 (CI 45370:1); D&C Orange 11 (CI 145425); FD&C Yellow 5 (CI 119140), FD&C Yellow 6 (CI 115985); D&C Yellow 10 (CI 147005); FD&C Green 3 (CI 142053); D&C Green 5 (CI 161570); FD&C Blue 1 (CI 142090); Cochineal Carmine (CI 175470); Guanine (CI 175170) and mixtures thereof.

The pearlescent pigments useful in the present invention include those selected from the group consisting of mica (or a similar plate-like substrate) coated with any of the following materials alone or in combination: titanium dioxide, bismuth oxychloride, iron oxides, ferric ferrocyamide, chromium oxide, chromium hydroxide, and any organic pigment of the above-mentioned type and mixtures thereof.

Film Forming Polymer

The compositions of the present invention may comprise a film forming polymer, for imparting wear and/or transfer resistant properties. When included, such materials are typically used in an amount of from about 0.5% to about 20% preferably from about 0.5% to about 10% by weight of the composition. Preferred polymers form a non-tacky film which is removable with water used with cleansers such as soap. The film forming polymers herein can be hydrophobic or hydrophilic, and can be provided in a lipophilic or aqueous carrier. When polymers provided in aqueous carriers are employed in the composition, a water-in-oil form is selected. Polymers of hydrophilic nature are also compatible with a water-in-oil form composition.

Examples of suitable film forming polymeric materials include:

a) sulfopolyester resins, such as those with tradename AQ sulfopolyester resins, such as AQ29D, AQ35S, AQ38D, AQ38S, AQ48S, and AQ55S available from Eastman Chemicals;
b) polyvinylacetate/polyvinyl alcohol polymers, such as tradename Vinex resins available from Air Products, including Vinex 2034, Vinex 2144, and Vinex 2019;
c) acrylic resins, including water dispersible acrylic resins available from National Starch under the trade name "Dermacryl", including Dermacryl LT;
d) acrylates and their derivative polymers, including acrylates copolymer with tradename Luvimer available from BASF, Avalure series available from Noveon, Daitosol 5000AD available from Daito Kasei Kogyo, ethylene.styrene/acrylates copolymer such as Syntran series available from Interpolymer, acrylates/ammonium methacrylate copolymer with tradename Ultrasol 2075C available from Presperse, octyl acrylates copolymer with tradename Daitotol SJ available from Kobo, acrylates silicone copolymer with tradename Daitotol ASC available from Kobo, AMP-acrylates/allyl methacrylate copolymer with tradename Fixate G100 Polymer available from Noveon, acrylate/dimethicone copolymer with tradename KP545 available from ShinEtsu;
e) styrene, such as sodium polystyrene sulfonate with tradename Flexan available from National Starch;
f) urethanes, such as polyurethane-1 polymer with tradename Luviset PUR available from BASF;
g) polyvinylpyrrolidones (PVP), including tradenames Luviskol K17, K30 and K90 available from BASF PVP K-30, PVP K-120 available from ISP, tricontanyl PVP with tradename Ganex WP 660 Resin available from ISP, water soluble copolymers of PVP, including PVP/VA S-630 and W-735 and PVP/dimethylaminoethylmethacrylate Copolymers such as Copolymer 845, Copolymer 937, and Styleze CC-10 available from ISP, VP/DAM available from Daiichi Kogyo Seiyaku, PVP/acrylates/lauryl methacrylate copolymer with tradename Styleze 2000 available from ISP;
h) high molecular weight silicones such as dimethicone and organic-substituted dimethicones, especially those with viscosities of greater than about 50,000 mPas;
i) high molecular weight hydrocarbon polymers with viscosities of greater than about 50,000 mPas such as polybutene, polybutene terephthalate, polydecene, polycyclopentadiene, and similar linear and branched high molecular weight hydrocarbons, including isooctane with tradename Permethyl 97A available from Presperse;
j) organosiloxanes, including organosiloxane resins, fluid diorganopolysiloxane polymers and silicone ester waxes.

Also useful herein are latex polymers including copolymer PVP/hexadecane or the copolymer PVP/eicosene marketed by ISP under the tradenames Ganex V-216® and Ganex V-220®, respectively. Ganex V-216® is a PVP/hexadecane copolymer comprising approximately 15-23% of pyrrolidone units with a weight average molecular weight of 7300. Ganex V-220® is a copolymer PVP/eicosene which comprises approximately 20-28% of pyrrolidone units and a weight average molecular weight of 8600.

Emulsifiers

The compositions of the present invention in emulsion form comprises an emulsifier, which is typically a lipophilic surfactant, preferably by weight of the entire composition at from about 1% to about 15%. The lipophilic surfactant herein has an HLB value of less than about 8.

The HLB value is a theoretical index value which describes the hydrophilicity-hydrophobicity balance of a specific compound. Generally, it is recognized that the HLB index ranges from 0 (very hydrophobic) to 40 (very hydrophilic). The HLB value of the lipophilic surfactants may be found in tables and charts known in the art, or may be calculated with the following general equation: HLB=7+(hydrophobic group values)+(hydrophilic group values). The HLB and methods for calculating the HLB of a compound are explained in detail in Surfactant Science Series, Vol. 1: Nonionic Surfactants", pp 606-13, M. J. Schick (Marcel Dekker Inc., New York, 1966).

Without being bound by theory, the species and levels of the lipophilic surfactant herein are believed to provide a stable water-in-oil emulsion in view of the other components of the present invention.

The lipophilic surfactant can be an ester-type surfactant. Ester-type surfactants useful herein include: sorbitan monoisostearate, sorbitan diisostearate, sorbitan sesquiisostearate, sorbitan monooleate, sorbitan dioleate, sorbitan sesquioleate, glyceryl monoisostearate, glyceryl diisostearate, glyceryl sesquiisostearate, glyceryl monooleate, glyceryl dioleate, glyceryl sesquioleate, diglyceryl diisostearate, diglyceryl dioleate, diglycerin monoisostearyl ether, diglycerin diisostearyl ether, and mixtures thereof.

Commercially available ester-type surfactants are, for example, sorbitan isostearate having a tradename Crill 6 available from Croda, and sorbitan sesquioleate with tradename Arlacel 83 available from Kao Atras.

The lipophilic surfactant can be a silicone-type surfactant. Silicone-type surfactants useful herein are (i), (ii), and (iii) as shown below, and mixtures thereof.

(i) dimethicone copolyols having the formulation:

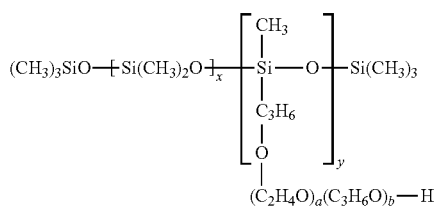

wherein x is an integer from 5 to 100, y is an integer from 1 to 50, a is zero or greater, b is zero or greater, the average sum of a+b being 1-100.

(ii) dimethicone copolyols having the formulation:

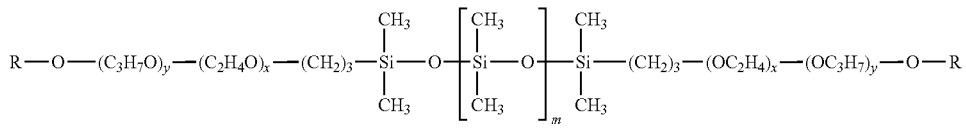

wherein R is selected from the group consisting of hydrogen, methyl, and combinations thereof, m is an integer from 5 to 100, x is independently zero or greater, y is independently zero or greater, the sum of x+y being 1-100.

(iii) branched polyether-polydiorganosiloxane emulsifiers herein having the formulation:

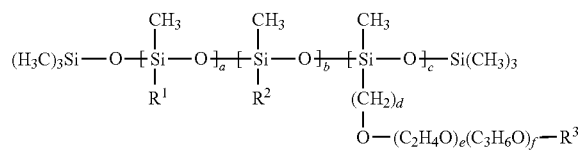

wherein $R^1$ is an alkyl group having from about 1 to about 20 carbons; $R^2$ is

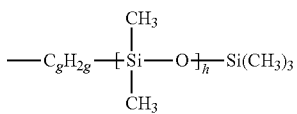

wherein g is from about 1 to about 5, and h is from about 5 to about 20; $R^3$ is H or an alkyl group having from about 1 to about 5 carbons; e is from about 5 to about 20; f is from about 0 to about 10; a is from about 20 to about 100; b is from about 1 to about 15; c is from about 1 to about 15; and d is from about 1 to about 5.

Commercially available silicone-type surfactants are, for example, dimethicone copolyols DC5225C, BY22-012, BY22-008, SH3746M, SH3771M, SH3772M, SH3773M, SH3775M, SH3748, SH3749, and DC5200, all available from Dow Corning, and branched polyether-polydiorganosiloxane emulsifiers such as PEG-9 polydimethylsiloxyethyl Dimethicone, having an HLB of about 4 and a molecular weight of about 6,000 having a tradename KF 6028 available from ShinEtsu Chemical.

Water

The composition of the present invention in water-in-oil form comprises water in an amount sufficient to provide a discontinuous aqueous phase, preferably an amount such that water is no more than about 50%, more preferably from about 10% to about 40% of the entire composition. Use of water allows the inclusion of useful components such as film forming polymers which are hydrophilic and/or aqueous carrier-based, hydrophilic conditioning agents, and other water soluble or water dispersible components described below.

In the present invention, deionized water is typically used. Water from natural sources including mineral cations can also be used, depending on the desired characteristic of the product.

Hydrophobic Conditioning Agents

The compositions of the present invention may further comprise a hydrophobic conditioning agent. Nonlimiting examples of hydrophobic conditioning agents include those selected from the group consisting of mineral oil, petrolatum, lecithin, hydrogenated lecithin, lanolin, lanolin derivatives, C7-C40 branched chain hydrocarbons, C1-C30 alcohol esters of C1-C30 carboxylic acids, C1-C30 alcohol esters of C2-C30 dicarboxylic acids, monoglycerides of C1-C30 carboxylic acids, diglycerides of C1-C30 carboxylic acids, triglycerides of C1-C30 carboxylic acids, ethylene glycol monoesters of C1-C30 carboxylic acids, ethylene glycol diesters of C1-C30 carboxylic acids, propylene glycol monoesters of C1-C30 carboxylic acids, propylene glycol diesters of C1-C30 carboxylic acids, C1-C30 carboxylic acid monoesters and polyesters of sugars, polydialkylsiloxanes, polydiarylsiloxanes, polyalkarylsiloxanes, cyclomethicones having 3 to 9 silicon atoms, polysiloxane crosspolymers such as vinyl dimethicone crosspolymer available as a dimethicone mixture fluid with tradename KSG series available from ShinEtsu, vegetable oils, hydrogenated vegetable oils, polypropylene glycol C4-C20 alkyl ethers, di C8-C30 alkyl ethers, and combinations thereof.

Hydrophilic Conditioning Agents

The compositions of the present invention may further comprise a hydrophilic conditioning agent. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3-C6 diols and triols, alpha-hydroxy C2-C6 carboxylic acids, ethoxylated and/or propoxylated sugars, polyacrylic acid copolymers, sugars having up to about 12 carbons atoms, sugar alcohols having up to about 12 carbon atoms, and mixtures thereof.

Solvents

The compositions of the present invention may contain a volatile or non-volatile solvent that dissolves or uniformly disperses certain components of the present invention. They include, but are not limited to, lower alcohols (such as ethanol, isopropanol), dihydric alcohols such as propylene and butylene glycol, polyols such as glycerin, hydroalcoholic mixtures, hydrocarbons (such as isobutane, hexane, decene, acetone), halogenated hydrocarbons (like Freon), linalool, hydrocarbon esters (such as ethyl acetate, dibutyl phthalate), volatile silicon derivatives, especially siloxanes (such as phenyl pentamethyl disiloxane, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof.

Additional Components

The compositions hereof may further contain additional components such as are conventionally used in topical products, e.g., for providing aesthetic or functional benefit to the composition or skin, such as sensory benefits relating to appearance, smell, or feel, therapeutic benefits, or prophylactic benefits (it is to be understood that the above-described required materials may themselves provide such benefits).

The CTFA Cosmetic Ingredient Handbook, Second Edition (1992) describes a wide variety of nonlimiting cosmetic and pharmaceutical ingredients commonly used in the industry, which are suitable for use in the topical compositions of the present invention. Such other materials may be dissolved or dispersed in the composition, depending on the relative solubilities of the components of the composition.

Examples of suitable topical ingredient classes include: sunscreen actives, anti-cellulite agents, antioxidants, radical scavengers, chelating agents, vitamins and derivatives thereof, abrasives, other oil absorbents, astringents, dyes, essential oils, fragrance, structuring agents, emulsifiers, solubilizing agents, anti-caking agents, antifoaming agents, binders, buffering agents, bulking agents, denaturants, pH adjusters, propellants, reducing agents, sequestrants, cosmetic biocides, and preservatives, such as propylparaben, methyl paraben, phenoxyethanol, benzyl alcohol, and EDTA and its salts.

Additional Usages

The cosmetic products herein may also be used for other usages in the personal care field, with necessary modifications to the composition and/or device suitable for the usage. Unlimited examples of such usages include coloring and treatment of eyebrows; treatment, styling, removing, and coloring of hair; treatment and tattooing of skin, and nail coloring.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Examples C1-C3

Examples C1 and C2 are mascara compositions in the form of oil mixture, and C3 is a mascara composition in the form of a water-in-oil emulsion. Each composition has a needle penetration of between 1-25 at 35° C., a yield stress of over 1500 Pa at 35° C., and has a viscosity of between 1 mPas and 10,000,000 mPas at 90° C. The mascara compositions can be suitably applied to the eyelashes when heated to between 50-80° C. via use of the device described hereinabove.

Composition

The following components are used at the respective w/w %.

| No. | Component | C1 | C2 | C3 |
|---|---|---|---|---|
| 1 | Glyceryl Monostearate-Vegetable Derived *1 | 8.00 | 10.00 | 10.00 |
| 2 | Stearyl Palmitate *2 | 26.00 | 18.00 | 17.00 |
| 3 | Ceresine Wax *3 | 26.00 | 18.00 | 17.00 |
| 4 | Paraffin Wax *4 | 15.50 | 9.70 | 7.87 |
| 5 | Dimethicone/Vinyl Dimethicone Crosspolymer *5 | | 25.00 | |
| 6 | Tricontanyl PVP *6 | 2.00 | 2.00 | 2.00 |
| 7 | Sorbitan Sesquioleate *7 | | | 5.00 |
| 8 | Propylparaben | 0.30 | 0.30 | 0.10 |
| 9 | CI 77499 (iron oxide) and Methicone *8 | 22.20 | 17.00 | 15.00 |
| 10 | Deionized Water | | | 20.00 |
| 11 | Sodium Polystyrene Sulfonate *9 | | | 5.00 |
| 12 | Phenoxyethanol | | | 0.30 |
| 13 | Methylparaben | | | 0.20 |
| 14 | Benzyl alcohol | | | 0.40 |
| 15 | Trisodium EDTA | | | 0.13 |

Definition of components:
*1 Glyceryl monostearate-vegetable derived: GMS-V available from Cognis
*2 Stearyl Palmitate: Purester 34 available from Strahl & Pitsch
*3 Ceresine wax: Ceresine Wax SP-252 available from Strahl & Pitsch
*4 Paraffin wax: Paraffin Wax SP-673P available from Strahl & Pitsch
*5 Dimethicone/Vinyl Dimethicone Crosspolymer: KSG 16 available from ShinEtsu
*6 Tricontanyl PVP: Ganex WP-660 available from ISP
*7 Sorbitan Sesquioleate: Crill 6 available from Croda
*8 CI 77499 (iron oxide) and Methicone: Si Black Iron Oxide available from Daito Kasei
*9 Sodium polystyrene sulfonate: Flexan II available from National Starch & Chemical Method of Preparation Examples C1-C3 may be made in any suitable method known to one skilled in the art. Preferably, the examples are made by the following methods.

Example C1

1) Heat components 1-4 to 85-90° C. Being low shear mixing when enough wax has melted.
2) Once components 1-4 have completely melted, add components 6 and 8. Continue mixing for about 10 min.
3) Add component 9 to product of Step 2, and disperse for 30 min-1 hr with a dispersator.
4) Pour the product of Step 3 into molds and allow product to cool and solidify.

Example C2

1) Heat components 1-4 to 85-90° C. Being low shear mixing when enough wax has melted.
2) Once components 1-4 has completely melted, add component 5. Continue mixing for about 10 min.
3) Add components 6 and 8 to product of Step 2. Continue mixing for about 10 min.
4) Add component 9 to product of Step 3, and disperse for 30 min-1 hr with a dispersator.
5) Pour the product of Step 4 into molds and allow product to cool and solidify.

Example C3

1) Heat components 1-4 to 85-90° C. Being low shear mixing when enough wax has melted.
2) Separately heat components 10-15 to 85-90° C. and mix with low shear mixing.
3) Once components 1-4 has completely melted, add components 6-8. Continue mixing for about 10 min.
4) Add component 9 to product of Step 3, and disperse for 30 min-1 hr with a dispersator 2. Homogenize for 30 min-1 hr by mixing.
5) Add the product of Step 2 to product of Step 4 while mixing with low shear mixing.
6) Further mix product of Step 5 with moderate shear mixing for 15-30 min. to effect emulsification.
7) Pour the product of Step 6 into molds and allow product to cool and solidify.

Examples C4-C5

Examples C4 and C5 are mascara compositions in the form of a hard core shell made by the composition of C1 described above, and inner core compositions as shown below. C4 is an aqueous continuous phase composition, and C5 is an oil continuous phase composition.

| Component | Inner core for C4 | Inner core for C5 |
|---|---|---|
| Paraffin wax | 2 | 10 |
| Bees wax | 2 | 5 |
| Carnauba wax | 4 | 5 |
| Synthetic wax | 6 | |
| Polyethylene wax | | 2 |
| Ceresin | | 5 |
| Trihydroxystearin | | 2 |
| Quaternium-18 hectorite | 5 | 8 |
| Propylene carbonate | 1 | 3 |
| Glyceryl monostearate | 7.5 | |
| Stearic acid | 1.7 | |
| Triethanolamine | 1.5 | |
| Polyvinyl alcohol | 1.5 | |
| Iron oxide | 10 | 12 |
| Propylparaben | 0.2 | 0.2 |
| Methylparaben | 0.2 | |
| Ethyl alcohol | 10 | |
| Water | 35.3 | |
| Acrylate Copolymer emulsion | 20 | |
| Volatile isoparaffin | | 37.8 |
| High molecular weight Dimethicone | | 10 |

Loading Mechanism of Mascara Treatment Device

Now, the details of the loading mechanism utilized in the present invention will be discussed with reference to several embodiments and their modifications.

First Embodiment

Figure 6:
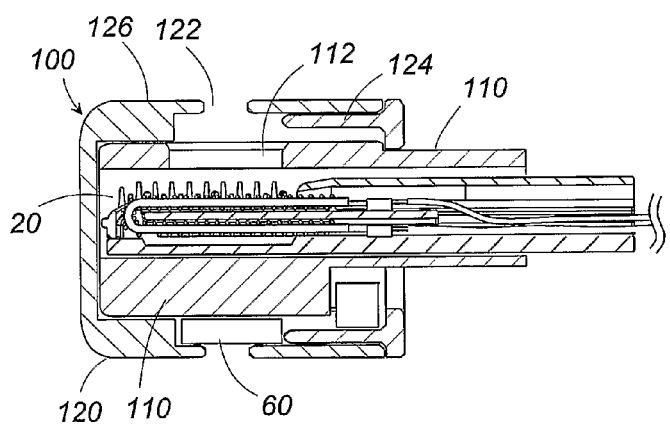
FIG. 6 is a front section of the cap.
Figure 7:
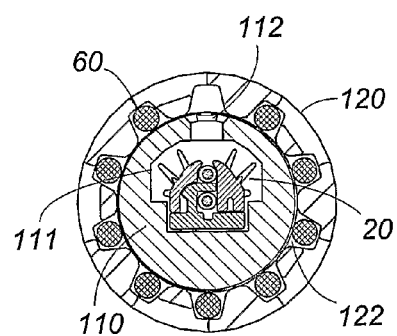
FIG. 7 is a side section of the cap.

FIGS. 5 to 7

Referring to FIGS. 5 to 7, there is shown a first embodiment of the loading mechanism provided on the side of the cap 100. The cap 100 includes a sheath 110 surrounding the applicator 20, and a carrier 120. The sheath 110 is formed with an opening 112 which comes into an open communication with the width center of the applicator 20 when the cap 100 is fitted over the applicator 60. The sheath 110 is shaped to have a non-circular bore 111 within which the applicator 20 is slidable but is rotatively fixed so that the applicator 20 has its widthwise center held into constant confrontation with the opening 112. The carrier 120 is in the form of a sleeve which is coaxial with the sheath 110 and is rotatable relative to the sheath 110. The carrier 120 is formed with a plurality of circumferentially spaced compartments 122 each storing the mascara piece 60. The carrier 120 is rotatable relative to the sheath to make one of the compartments 122 selectively in registration with the opening for allowing the mascara piece 60 to drop onto the applicator 20 through the opening 112, thereby loading the mascara piece one by one to the applicator 20. The carrier 120 is composed of a rotating shell 124 rotatably coupled to the sheath 110, and a jacket 126 forming outer bottoms of the compartments 122. The compartments 122 are defined between the shell 124 and the jacket 126. The jacket 126 may be configured to be detachable to the shell 124, enabling to refill the mascara pieces by removal of the jacket 126.

Figure 8:
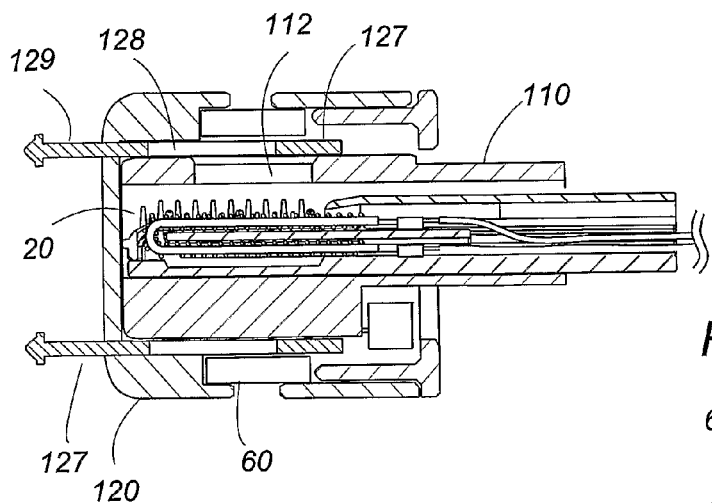
FIGS. 8 and 9 are front section and side section showing a cap in accordance with a modification of the first embodiment.
Figure 9:
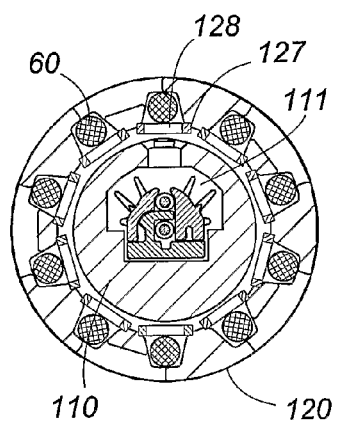

FIGS. 8 and 9 show a modification of the above loading mechanism which is identical to the above embodiment except for the provision of a gate 127 to each of the compartments 122. Each gate 127 is held slidable in the axial direction of the carrier 120, and has its one end projected beyond the end of the carrier 120 to define thereat an operator knob 129.

The gate 127 has a through-hole 128 and is normally held in a closing position of closing the associated compartment 122 for prohibiting the mascara piece 60 from dropping through the opening to the applicator 20. When the gate 127 is pushed axially inward, the compartment 122 is opened to allow the mascara piece 60 to drop by way of the through-hole 128 and the opening 112 to the applicator 20. Alternatively, it may be arranged that a single gate is provided on the side of the carrier 110 rather than the carrier 120.

Figure 10:
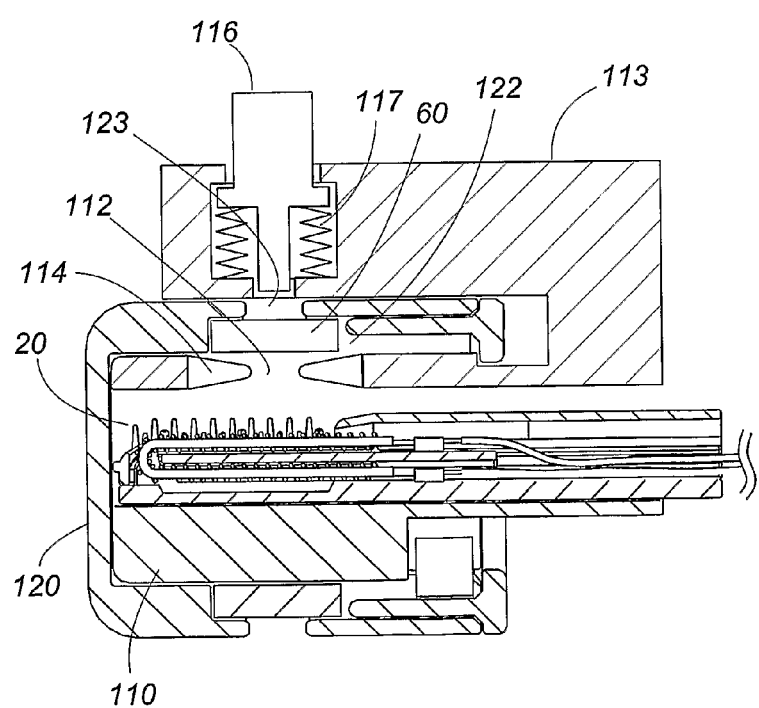
FIG. 10 is a front section showing a cap in accordance with another modification of the first embodiment.
Figure 11:
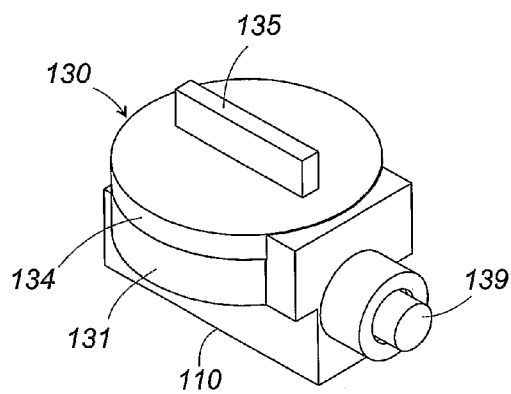
FIG. 11 is a perspective view of a cap in accordance with a second embodiment of the present invention.
Figure 12:
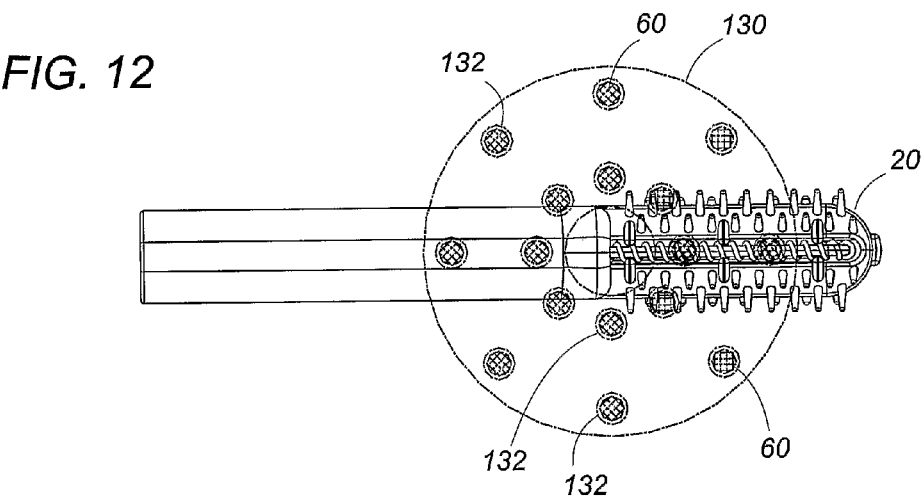
FIGS. 12 and 13 are horizontal section and front section showing the cap.
Figure 13:
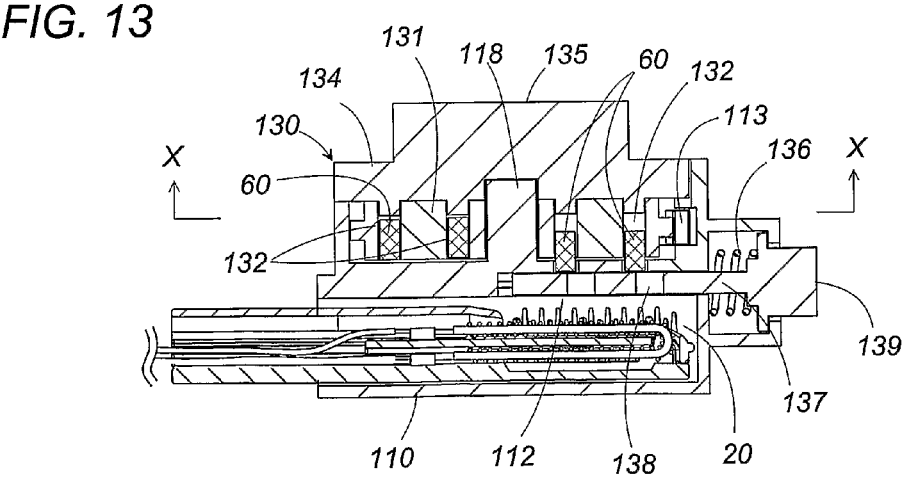

FIG. 10 shows another modification of the above loading mechanism which is identical to the above embodiment except for a provision of a plunger 116 which is configured to force the mascara piece 60 out of the compartment 122. The opening 112 is equipped with a normally-closed flap valve 114 for retaining the mascara piece 60 within the compartment 122 even when any one of the compartment comes into registration with the opening 112. The plunger 116 is supported to an extension 113 of the sheath 112 so as to be radially movable relative to the sheath 110 for advancing its inner radial end for pushing contact with the mascara piece 60 through an aperture 123 in the exterior wall of the carrier 120. When the plunger 116 is pushed against a bias of spring 117, it forces the mascara piece 60 radially inward, thereby temporarily opening the flap valve 114 and accordingly loading the mascara piece 60 to the applicator 20. Upon releasing the plunger 116 after loading the mascara piece 60, the flap valve 114 returns by its resiliency to the closed position.

Second Embodiment

FIGS. 11 to 14

FIGS. 11 to 14 illustrate a second embodiment of the loading mechanism which is similar to the above embodiment except for the provision of the carrier in the form of a disc 130 which is supported to the sheath 110 to be rotatable relative thereto about an axis perpendicular to the lengthwise axis of the sheath 110. The disc 130 is composed of a base 131 and a jacket 134 which are secured together to define therebetween a plurality of circumferentially spaced compartments 132 for holding the mascara pieces 60, respectively. The disc 130 is mounted around a spindle 118 integrally projecting on top of the sheath 110 to be rotatable about the axis of the stud. The compartments 132 are arranged into two circumferential arrays such that each compartment in one of the arrays is radially aligned with each corresponding one in the other array in order to deliver the two mascara pieces 60 simultaneously to the two longitudinally spaced spots on the applicator 20 through the opening 112 elongated axially along the axis of the sheath 110. The compartments 132 are open in the lower surface of the disc 130 to be in communication with the opening 112 in the sheath 110. The sheath 110 is additionally formed with a gate 137 slidable along the axis of the sheath 110 so as to normally close the bottoms of the compartments 132 coming into registration with the opening 112, retaining the mascara pieces within the disc 130. The gate 137 is formed at its lengthwise end with an operation knob 139 to be accessible by a user's finger. When the knob 139 is pressed against a bias of a spring 136 to move the gate axially inwardly, through-holes 138 in the gate come into open communication with the compartments 132, thereby permitting the mascara pieces 60 to drop onto the applicator 20 by way of the through-holes 138 and the opening 112.

Figure 14:
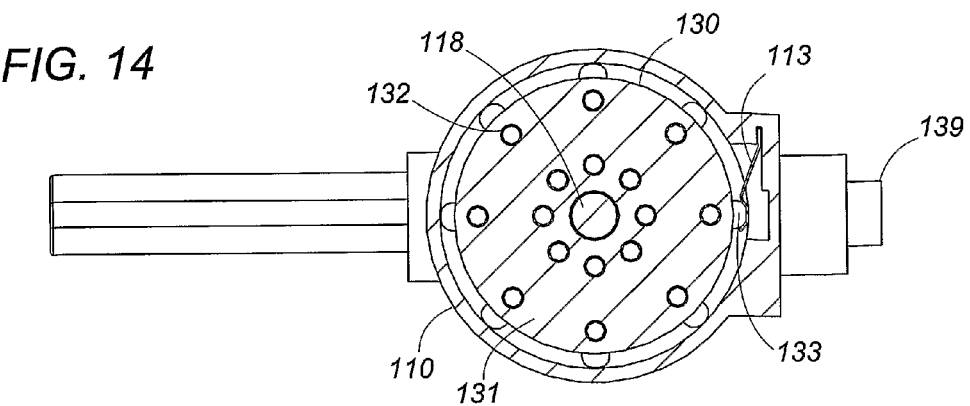
FIG. 14 is a cross section taken along line X-X of FIG. 13.

The jacket 134 is formed on its top with handle 135 for rotating the disc 130. As shown in FIG. 14, a catch spring 113 is provided on the side of the sheath for selective latching engagement with any one of latch projections 133 on the periphery of the disc 130, giving a clicking rotary motion to the disc 130. The jacket 134 may be detachable to the base 131 for allowing the refilling of the mascara pieces.

Although the illustrated embodiment discloses that the two compartments come simultaneously into registration with the opening at one time, it is equally possible to arrange the compartments such that a single compartment or more than two compartments come into registration with the opening.

Third Embodiment

Figure 15:
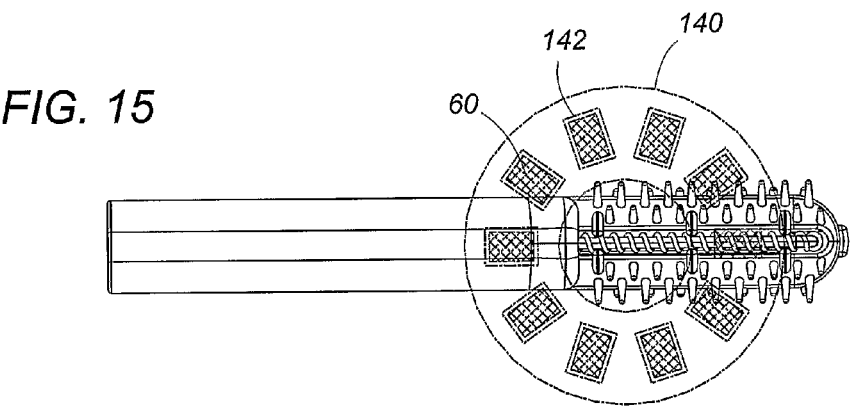
FIGS. 15 and 16 are horizontal section and front section showing a cap in accordance with a third embodiment of the present invention.
Figure 16:
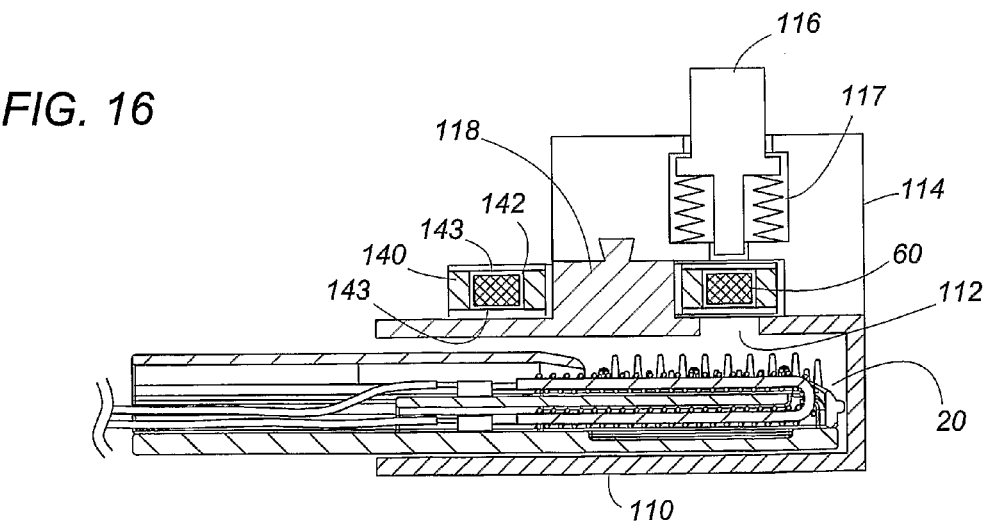

FIGS. 15 and 16

FIGS. 15 and 16 illustrates a third embodiment of the loading mechanism which is similar to the second embodiment except that the disc 140 is alone provided as a replacement part detachable to the sheath 110 and each compartment 142 is sealed at its upper and lower ends with breakable seals 143 to retain the mascara pieces 60 in the compartment. The disc 140 is detachably mounted around a spindle 118 projecting on the periphery of the sheath 110 to be rotatable about an axis perpendicular to the axis of the sheath 110. The compartments 142 are circumferentially spaced and are each sealed at its upper and lower open ends respectively by the breakable seals 143 in the form of aluminum foils, for example, to retain therein the mascara piece 60. The sheath 110 is additionally formed with a detachable base 114 which carries a plunger 116 movable in a direction perpendicular to the axis of the sheath 110. When the plunger 116 is pressed against the bias of a spring 117, it breaks the seal 143 and forces the mascara piece 60 out of the compartment 142, thereby allowing the mascara piece 60 to drop onto the applicator through the opening 112 of the sheath 110. When the disc 140 is exhausted of the mascara piece 60, it is replaced by a fresh disc filled with the mascara pieces.

Fourth Embodiment

FIG. 17

Figure 17:
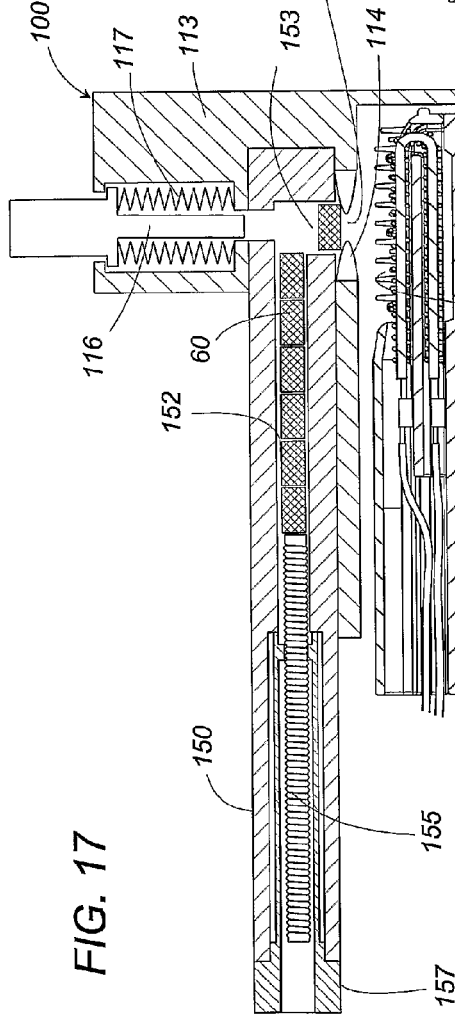
FIG. 17 is a front section of a cap in accordance with a fourth embodiment of the present invention.

FIG. 17 illustrates a fourth embodiment of the loading mechanism provided on the side of the cap 100. The cap 100 includes a sheath 110 configured to accommodate the device, and a holder in the form of a tube 150 which runs parallel to the sheath along the length of the applicator to define therein an elongated compartment 152 for receiving therein a series of mascara pieces 60. An outlet 153 is formed in the periphery of the tube 150 adjacent to one axial end thereof to deliver the mascara piece 60 onto the applicator 20 through an opening 112 formed in the sheath 110. A screw-in-piston 155 is inserted in the tube 150 to advance the mascara pieces 60 towards the outlet 153. The tube 150 is provided at its axial end remote from the outlet 153 with a dial 157 of which rotational motion is translated into a linear motion of the screw-in-piston 155 within the tube 150. Thus, rotating the dial 157 in one direction advances the piston 155 and therefore the mascara pieces 60 towards the outlet 153. The mascara piece 60 reaching the outlet 153 is caused to drop into the opening 112 and is retained thereat by means of normally-closed flap valves 114. A plunger 116 is provided to force the mascara piece 60 out of the opening 112 by temporarily opening the valves 113, allowing the mascara piece 60 to drop onto the applicator 20. The plunger 116 is supported to an extension 113 of the sheath to be movable in a direction perpendicular to the axis of the tube 150. When pressed against the bias of a spring 117, the plunger 116 has its lower end projected into the tube 150 and into the outlet 153, forcing the mascara piece 60 out of the opening 112. Refilling of the mascara pieces is made by removing the dial 157 and the piston 155 out of the tube 150. The tube 150 may be detachable to the sheath 110 as a replacement part containing a plurality of mascara pieces 60.

Figure 18:
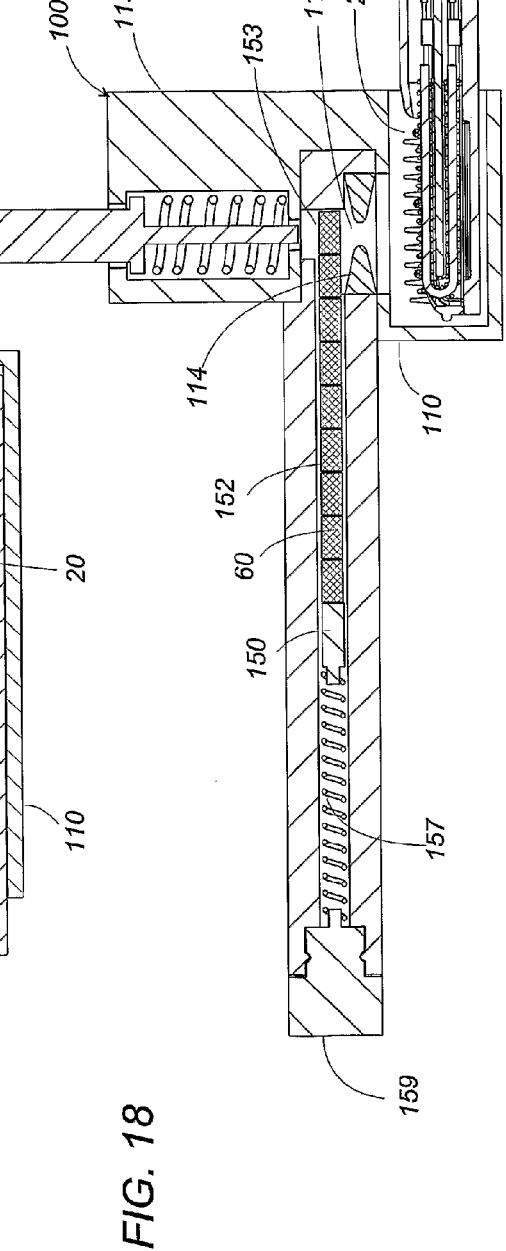
FIG. 18 is a front section of a cap in accordance with a modification of the fourth embodiment.

FIG. 18 illustrates a modification of the above embodiment which is identical to the fourth embodiment except for the use of a spring-biased piston 155 in place of the screw-in-piston. The piston 156 is disposed within the tube 150 together with a spring 157 which biases the piston 155 to feed the mascara pieces 60 towards the outlet 153. An end cap 159 is held in a threaded engagement with one end of the tube 150 to bear the spring 157. Like parts are designated by like reference numerals for easy reference purpose.

Fifth Embodiment

FIG. 19

Figure 19:
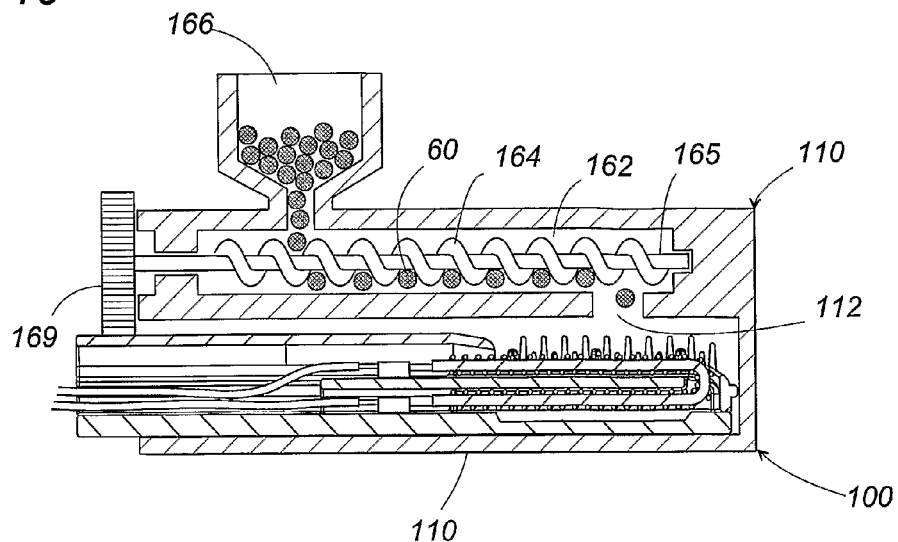
FIG. 19 is a front section of a cap in accordance with a fifth embodiment of the present invention.

FIG. 19 illustrates a fifth embodiment of the loading mechanism provided on the side of the cap 100. The cap 100 includes a sheath 110 configured to receive the device and to have an elongated compartment 162 extending in parallel with an axis of the sheath 110. The compartment 162 accommodates therein a screw-conveyer 164 which feeds the mascara pieces 60 in the form of pellets supplied at a hopper 166 towards an opening 112 formed at one axial end of the sheath 110. The opening 112 is disposed adjacent to the applicator 20 for delivering the mascara pieces onto the applicator 20. The screw-converter 164 is composed of an axle 165 with a spiral fin and is rotatably supported to the sheath 110. A dial 169 is coupled to the axle 165 for rotating the conveyor 164 and therefore feeding the mascara pieces 60 to the applicator 20 out through the opening 112.

Figure 23:
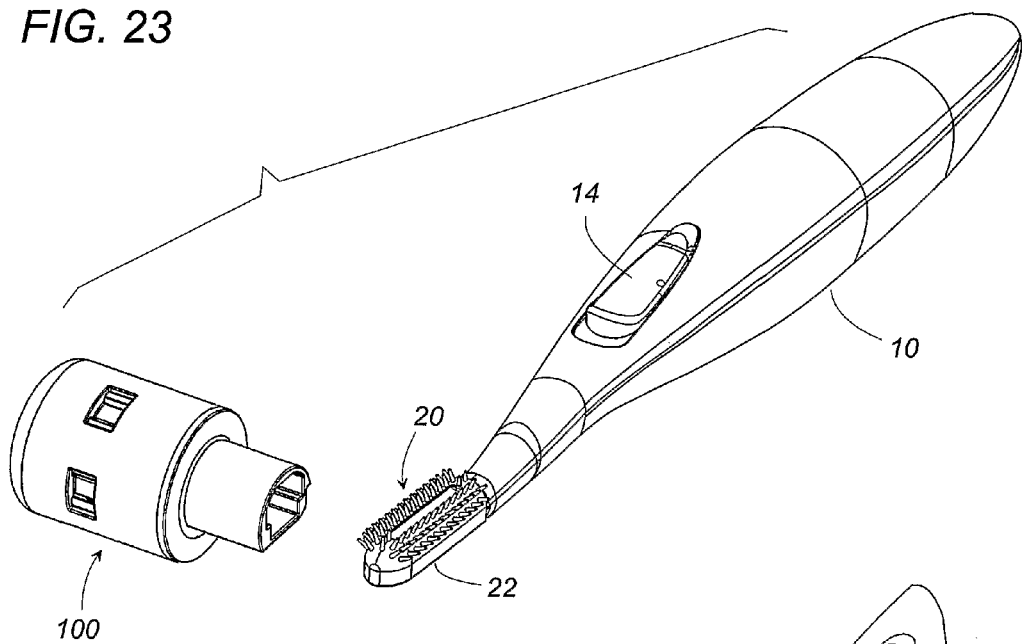
FIGS. 23 and 24 are exploded perspective views of another eyelash treatment device which can be equally utilized in the present invention.
Figure 24:
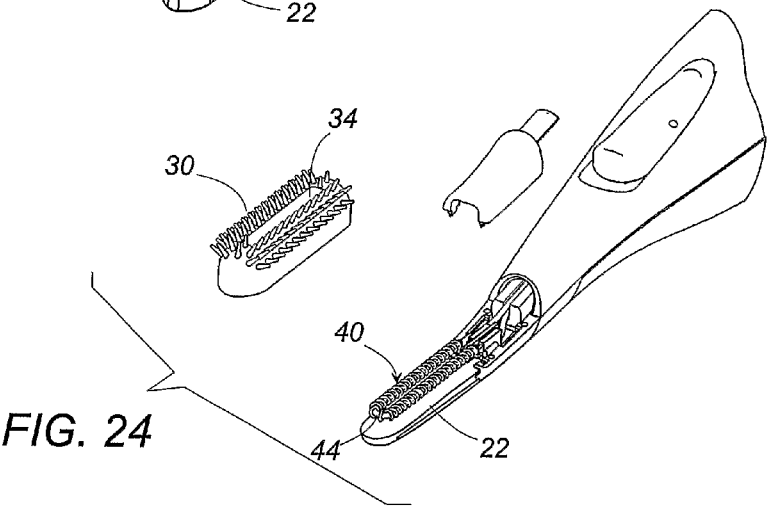
Figure 25:
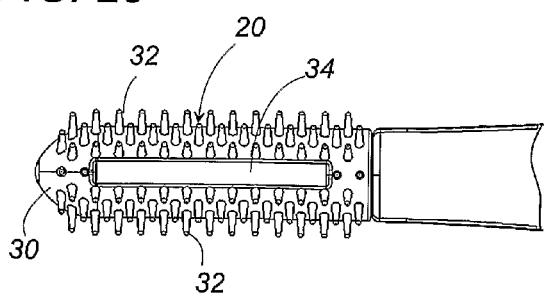
FIG. 25 is a partial top view of the applicator of the above device.
Figure 26:
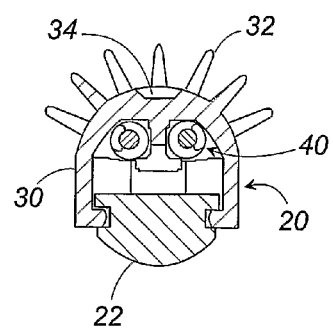
FIG. 26 is a cross section of the applicator.

FIGS. 23 to 24 illustrate an eyelash treatment device which may be equally utilized in combination with various mascara feeding caps as discussed hereinbefore. Like parts are designated by like reference numerals for easy reference purpose. The device has a grip 10 and an applicator 20, which is composed of a head 22 extending integrally from the grip 10, and a comb attachment 30 detachably fitted on the head 22. The head 22 is made of a dielectric plastic material and carries the heater 40 composed of a resistor coil 42 wound around a U-shaped core 44 of dielectric material to give two parallel horizontal rows running in the length of the applicator 20. The coil 42 is electrically connected to a voltage source, i.e., a battery 12 within the grip 10 and is energized by manipulating a switch handle 14 on the side of the grip 10. The comb attachment 30 is made of a dielectric plastic material and is fitted on the head 22 in thermal contact with the heater 40 so as to be heated at an elevated temperature for softening the mascara composition. The comb attachment 30 is shaped to have a rounded top face provided with a comb having a plurality of comb teeth 32 which are arranged along the length and width of the applicator for applying the softened mascara composition to the eyelashes while smoothening the eyelashes. A ditch 34 is formed in the width center of the top face to extend the length of the applicator 20 for receiving the mascara piece 60 and retaining the softened mascara composition, which is thereafter allowed to flow over the comb teeth. The softened mascara composition climbs-up to the comb teeth 32 by the action of a surface tension to be ready for being delivered to the eyelashes as the comb teeth 32 smoothen the eyelashes.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An eyelash treatment device comprising:
a grip to be grasped by a user's hand;
an applicator configured to be supported by said grip and to receive a mascara composition for delivering said mascara composition to eyelashes of the user; and
a cap configured to fit over said applicator and hold said mascara composition,
wherein said cap is provided with a means for loading which is configured to hold a plurality of pieces of said mascara composition and to load the pieces one by one to said applicator,
wherein said cap includes a sheath fitted around the applicator and being formed with an opening communicating with said applicator, and
wherein the piece of said mascara composition is loaded to said applicator through said opening.

2. The eyelash treatment device as set forth in claim 1, wherein said applicator is elongated to have a length and carrying:
a heater extending along said length for softening said mascara composition by heat, and
a comb being arranged along the length of said applicator to be coated with the softened mascara composition for delivering to the eyelashes.

3. The eyelash treatment device as set forth in claim 1 or 2, wherein said means for loading includes a carrier which is formed with a plurality of compartments each storing said piece of said mascara composition, said carrier being movable relative to said sheath to make one of the compartments selectively in registration with said opening for loading the piece of said mascara composition to said applicator through said opening.

4. The eyelash treatment device as set forth in claim 3, wherein said sheath is configured to be rotatively fixed relative to said applicator, and to have an axis extending along a length of said applicator; said carrier being in the form of a sleeve coaxial with said sheath and having said compartments arranged circumferentially about said axis, and said sleeve being rotatable about said axis relative to said sheath.

5. The eyelash treatment device as set forth in claim 4, wherein said sleeve includes a plurality of gates respectively closing said compartments, each of said gates being movable to open each associated one of said compartments for loading the piece of said mascara composition into said applicator.

6. The eyelash treatment device as set forth in claim 4, wherein
said opening is provided with a normally-closed flap valve,
said means for loading includes a plunger which forces the piece of said mascara composition to temporarily open said flap valve for loading the same into said applicator.

7. The eyelash treatment device as set forth in claim 3, wherein
said sheath is configured to be rotatively fixed relative to said applicator and to have an axis extending along a length of said applicator;
said carrier is in the form of a disc rotatable relative to said sheath about an upright axis perpendicular to the axis of said sheath, and
said disc having the plurality of said compartments circumferentially arranged about said upright axis.

8. The eyelash treatment device as set forth in claim 7, wherein said means for loading includes a gate which normally closes the opening of said sheath, said gate being movable to an open position for loading the piece of said mascara composition from said compartment into said applicator.

9. The eyelash treatment device as set forth in claim 7, wherein
each piece of said mascara composition is retained in each of said compartments by means of a breakable seal,
said means for loading includes a plunger which forces the piece of said mascara composition out of said breakable seal so as to load the same to said applicator.

10. The eyelash treatment device as set forth in claim 7, wherein
said opening is elongated along the axis of the sheath,
said disc is formed with a plurality of said compartments which are spaced circumferentially and radially such that a set of radially aligned compartments comes into registration with said axially arranged openings.

11. The eyelash treatment device as set forth in claim 1 or 2, wherein
said cap comprises a compartment which extends along a length of said applicator for receiving a plurality of pieces of said mascara compositions in series,
one length end of said compartment communicates with said applicator through said opening, said opening being provided with a normally-closed flap valve,
said means for loading including a feeder in the form of a screw-in piston that drives the pieces of said mascara composition linearly within said compartment towards said opening,
said means for loading further comprising a plunger that forces the piece around said opening against said flap valve to temporarily open the same, thereby loading the piece of said mascara composition into said applicator through said opening.

12. The eyelash treatment device as set forth in claim 1 or 2, wherein
said cap comprises a compartment which extends along a length of said applicator for receiving a plurality of pieces of said mascara compositions in series,
said compartment being formed at its one lengthwise end with said opening which communicates with said applicator, said opening being provided with a normally-closed flap valve,
said means for loading including a feeder in the form of a spring-biased piston that drives the pieces of said mascara composition linearly within said compartment towards said opening,
said means for loading further including a plunger which forces the piece around said opening against said flap valve to temporarily open the same, thereby loading the piece of said mascara composition into said applicator through said opening.

13. The eyelash treatment device as set forth in claim 1 or 2, wherein
said cap comprises a compartment extending along a length of said applicator,
said sheath being formed at its one lengthwise end with said opening through which said compartment communicates with the applicator,
said means for loading including a hopper which is formed at the other lengthwise end of said sheath to receive said pieces in the form of pellets,
said means for loading including a screw conveyor that extends into said compartment so as to feed the pellets from said hopper to said opening for loading the same into said applicator.

14. A cosmetic product comprising the eyelash treatment device as set forth in claim 1,
the cosmetic product comprises a mascara composition comprising at least a solid hydrophobic component; said mascara composition having:
i) a needle penetration, as measured according to the ASTM Test Method D5, of from about 1 to about 40 at 25° C.;
ii) a yield stress of at least about 1500 Pa at 25° C.;
iii) a viscosity of between about 1 mPas and about 10,000,000 mPas at 100° C.

* * * * *